United States Patent
Schroder et al.

(10) Patent No.: US 6,890,540 B1
(45) Date of Patent: May 10, 2005

(54) VACCINE FORMULATION

(75) Inventors: Ulf Schroder, Sundbyberg (SE); Stefan Svenson, Enskede (SE)

(73) Assignee: Eurocine AB, Stockholm (SE)

( * ) Notice: Subject to any disclaimer, the term of this patent is extended or adjusted under 35 U.S.C. 154(b) by 178 days.

(21) Appl. No.: 09/926,002

(22) PCT Filed: Feb. 9, 2000

(86) PCT No.: PCT/EP00/01038

§ 371 (c)(1),
(2), (4) Date: Oct. 30, 2001

(87) PCT Pub. No.: WO00/47224

PCT Pub. Date: Aug. 17, 2000

(30) Foreign Application Priority Data

Feb. 12, 1999 (SE) ............................................... 9900496

(51) Int. Cl.$^7$ ..................... A61K 39/04; A61K 39/00; G01N 33/53
(52) U.S. Cl. ................. 424/248.1; 424/184.1; 424/283.1; 424/435; 424/7.1; 424/7.2
(58) Field of Search ........................... 424/184.1, 248.1, 424/283.1; 435/7.1, 7.2

(56) References Cited

U.S. PATENT DOCUMENTS

| 6,350,456 B1 | * | 2/2002 | Reed et al. | 424/248.1 |
| 6,451,325 B1 | * | 9/2002 | Van Nest et al. | 424/283.1 |

FOREIGN PATENT DOCUMENTS

| WO | EP 0 448 126 A | 9/1991 |
| WO | WO 97 35613 A | 10/1997 |
| WO | WO 97/35613 | * 10/1997 |
| WO | WO 97 47320 A | 12/1997 |
| WO | WO 97/47320 | * 12/1997 |

OTHER PUBLICATIONS

Vercellone et al, Frontiers in Bioscience, Aug. 6, 1998;3:149–63.*
Hansen et al, Ann Surg, Jul. 1976: 184(1):80–88.*
Hamasur et al, Vaccine, 17, 1999, 2853–2861.*
Vercellone et al, Frontiers in Bioscience, Aug. 6, 1998;3:e149–63.*

* cited by examiner

Primary Examiner—James O. Wilson
Assistant Examiner—Vanessa L. Ford
(74) Attorney, Agent, or Firm—Bacon & Thomas

(57) ABSTRACT

A vaccine formulation against a microorganism is disclosed. The formulation comprises: as adjuvant, one or more substances selected from a) monoglyceride preparations having at least 80% monoglyceride content and b) fatty acids of the general formula $CH_3-(CH^2)_n-COOH$ where "n" may be varied between 4 and 22, and where the acyl chain may contain one or more unsaturated bonds, and as immunizing component, an immunogenic product consisting of antigenically active carbohydrate moieties (ACM) derived from said microorganism which are each covalently coupled, possibly via identical divalent bridge groups, to immunologically active carriers (IAC). The vaccine formulation is e.g. against *Mycobacterium tuberculosis* and in that case the formulation may comprise, as adjuvant, a mixture of mono-olein and oleic acid, and possibly soybean oil, and, as immunizing component, lipoarabinomamman-tetanus toxoid (LAM-TT).

40 Claims, 1 Drawing Sheet

VACCINE FORMULATION

Figure 1:
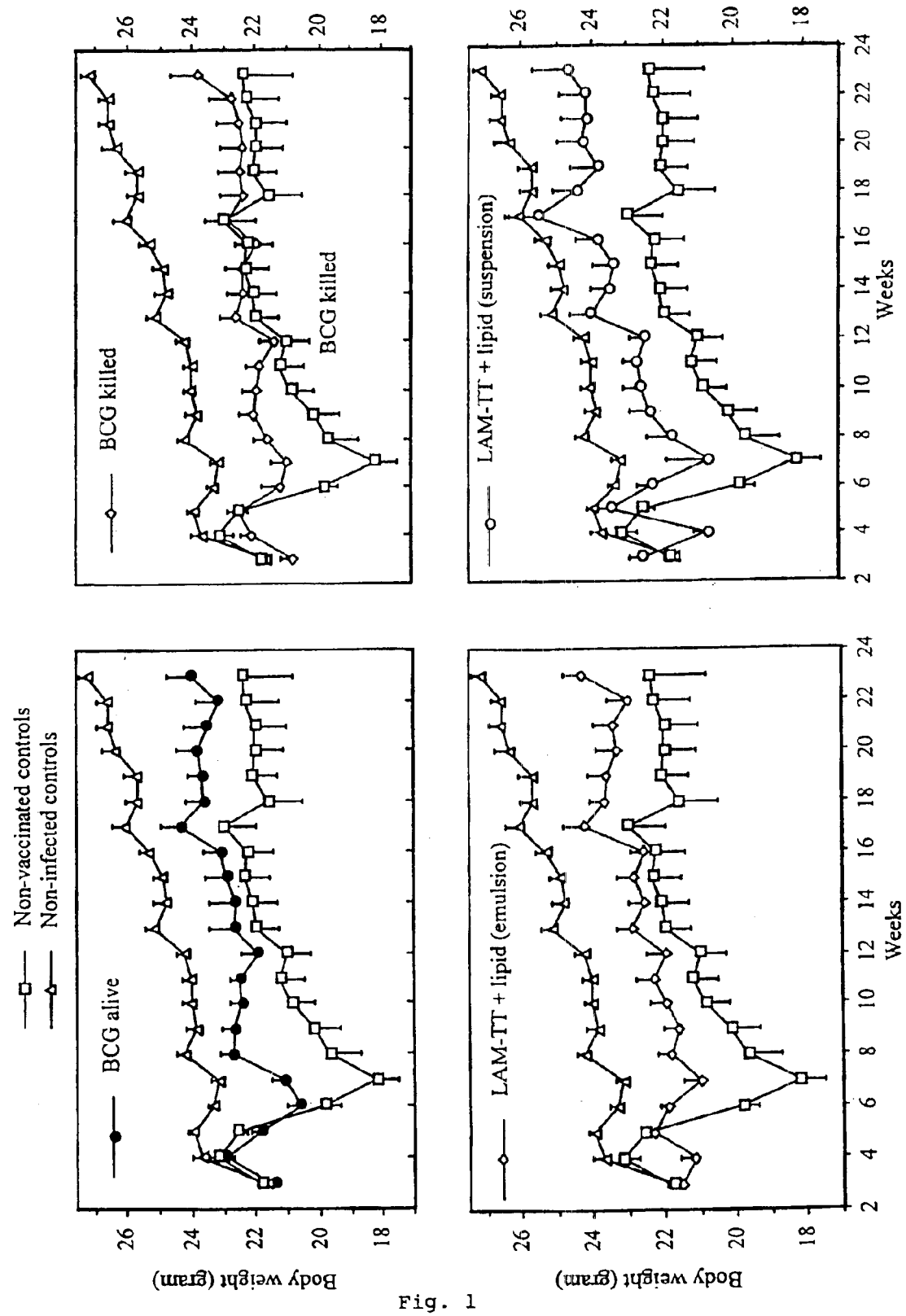

This application claims priority to a 371 of PCT/EP00/01038, filed 9 Aug. 2000.

The present invention relates to a novel vaccine formulation against a microorganism e.g. *Mycobacterium tuberculosis*. The preferred route of administration is via the mucosal membranes.

BACKGROUND

The earliest described immunization attempts were carried out in China over 900 years ago, where intranasal inoculation of dried and ground smallpox pustules was performed. In the classical immunology and in combination with vaccination against different types of infectious agents e.g. bacteria, virus or parasites the prevailing dogma has been to administer the vaccine subcutaneously or intramuscularly. However, research has during the last years shown that the body has a very effective immunological system that resides in the mucosa. It has also been shown that you can administer vaccines nasally, orally, rectally and vaginally. In the same way as for the classical immunization it has been shown that by mucosal vaccination there is also a need for enhancement of the immunological response by the addition of adjuvants.

The intranasal route has attracted increased attention because of the greater efficacy in inducing mucosal immune responses than the more conventional regimes of parenteral immunization. Furthermore, the realization that approximately 80% of the immune system reside in the mucosa combined with the fact that an equal percentage of the known pathogens enter our bodies via the mucosal membranes has pushed the interest towards the application of mucosal immunization.

It has also been shown that parenteral vaccines do not induce immune response at mucosal sites. Thus, it is also clear that appropriate stimulation of a mucosal site such as the nose or the gut, can generate immune response in other mucosal sites. As an example, it is possible to apply a vaccine in the nose and obtain an immune response in the vagina. Furthermore, the mucosal immune response is very rapid with onset only hours after being subjected to stimulation by a pathogen, as compared to parenteral immunity having a response time of several days.

Tuberculosis (TB) is one of the major causes of morbidity in the world with an estimated death toll of approximately 3 millions per year. It is estimated that ⅓ of the world's population is infected with TB. To a large extent TB is essentially an uncontrolled problem despite the use of the Bacille Calmette-Guérin (BCG) vaccine for more than 75 years.

The BCG vaccine consists of a weakened strain of a tuberculosis bacteria taken from a cow in 1908. The original bacteria used today were cultured for 13 years for the purpose of weaken their pathogenic characteristics in order to be used as live bacteria for parenteral vaccination of humans. Basically the same strain is used today as the only vaccine available against TB. Several pharmaceutical companies around the world produce the BCG vaccine. The BCG formulation used today consists of freeze-dried attenuated viable BCG vaccine in one container and another container with physiologically acceptable suspension media. Before administration, the freeze-dried BCG is suspended and subsequently administered by injection to the patient. This procedure which has to be carried out immediately in connection with the vaccination, requires skilled personnel and decent facilities in order to avoid contamination. Unfortunately these criteria are hard to keep up with in the developing countries. Thus, it is estimated that failure to keep to this standard costs about USD 500 millions each year world-wide. Consequently, huge savings could be made both in money and product safety, if a system was available where no mixing of vaccines was needed and where injections could be eliminated, thus eliminating the need for highly skilled personnel and sterile conditions.

In clinical trails around the world, the protective efficacy of the BCG vaccine has been shown to vary between −50% to +80%. This means that certain clinical studies have shown that in fact you enhance instead of diminish your risk of getting the disease after vaccination.

The BCG vaccine works well for children but has more or less no effect on adults. Consequently there are great efforts made in order to achieve a vaccine against TB for the grown-up population. Up to date however, there are no reports in the literature of a TB vaccine that is better than BCG.

Tuberculosis is spread by close person-to-person contact through infectious aerosols. On rare occasions the disease can be acquired by ingestion or skin trauma. This means that the first organ to get into contact with the bacteria during a normal infection is the mucosal surfaces in the lungs.

Adjuvants are a heterogeneous group of substances that enhance the immunological response against an antigen that is administered simultaneously.

Almost all adjuvants used today for enhancement of the immune response against antigens are particles or are forming particles together with the antigen. In the book "Vaccine Design—the subunit and adjuvant approach" (Ed: Powell & Newman, Plenum Press, 1995) almost all known adjuvants are described both regarding their immunological activity and regarding their chemical characteristics. As described in the book more than 80% of the adjuvants tested today are particles or polymers that together with the antigens (in most cases proteins) are forming particles. The type of adjuvants that are not forming particles are a group of substances that are acting as immunological signal substances and that under normal conditions consist of the substances that are formed by the immune system as a consequence of the immunological activation after administration of particulate adjuvant systems.

Using particulate systems as adjuvants, the antigens are associated or mixed with or to a matrix, which has the characteristics of being slowly biodegradable. Of great importance using such matrix systems are that the matrices do not form toxic metabolites. Choosing from this point of view, the main kinds of matrices that can be used are mainly substances originating from a body. With this background there are only a few systems available that fulfill these demands: lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are the most important part in all biological membranes.

Lipids are characterized as polar or non-polar. The lipids that are of most importance in the present invention are the polar lipids since they have the capacity to interact and form particulate systems in water. Another way of defining these lipids are as amphiphilic due to their chemical structure with one hydrophobic and one hydrophilic part in the molecule thereby being useable as surface active substances. Examples of main groups of polar lipids are monoglycerides, fatty acids, phospholipids and glycosphingolipids. These main groups can be further characterized depending on the length of the acyl chain and the degree of saturation of the acyl chain. Since the number of carbon atoms in the acyl chain can be in the range of 6 to 24, and the number of unsaturated bonds can be varied, there is an almost infinite number of combinations regarding the chemical composition of the lipid.

Particulate lipid systems can be further divided into the different groups as discussed in the scientific literature such as liposomes, emulsions, cubosomes, cochleates, micelles and the like.

In a number of systems the lipids may spontaneously form, or can be forced to form, stabile systems. However, under certain circumstances other surface-active substances have to be introduced in order to achieve stability. Such surface-active systems can be of non-lipid character but possess the characteristics of the polar lipids having hydrophobic and hydrophilic parts in their molecular structure.

Another factor that has been shown to be of importance is that lipids exhibit different physical chemical phases, these phases have in different test systems been shown to enhance uptake of biological substances after administration to mucous membranes. Examples of such physical chemical phases described are L2, lamellar, hexagonal, cubic and L3.

In the same way as within the classical immunology where vaccines (antigens) are administered parenterally, there is within mucosal immunization a great interest in directing the immunological response towards development of humoral and/or cellular response. If you obtain a humoral response it would be important to direct the response in a way that a certain class of antibodies would be obtained. In order to obtain such a goal, specific immune stimulating agents can be added to the formulation of antigens and adjuvants.

A formulation which fulfils these goals is described in PCT/SE97/01003, the contents of which is incorporated herein by reference. The disclosed formulation comprises monoglycerides and fatty acids. The monoglycerides comprise one or more substances selected from monoglycerides wherein the acyl group contains from 6 to 24 carbon atoms, preferably 8 to 20 carbon atoms, even more preferably 14–20 carbon atoms and where the acyl chain may contain unsaturated bonds.

The acyl chain of the fatty acid may be varied between 4 and 22, preferably 8 to 18 and where the acyl chain may contain one or more unsaturated bonds. A combination of the monoglyceride mono-olein and oleic acid has shown to be an L3 phase, which can be described as sponge-like structure, in contrast to liposomes that form onion-like lamellar structures.

Said combination of monoglycerides and fatty acids my be further formulated by the addition of a biocompatible and biodegradable oil thus forming an oil in water (o/w) or w/o/w emulsion. Such emulsions have been shown in the literature to be very effective in enhancing the cellular response against an antigen after administration to an animal (Singh, M., et al 1997, *Vaccine* 15, 1773–78). It is generally accepted that in order to have an acceptable vaccine against TB there is a need for a cellular immune response.

Thus, there is a need for a simple way of administering a vaccine combined with an antigen that is easily documented and formulated. One way of producing such a system would be to use antigenic surface components from bacteria which would have the capacity to provoke an immune response in a body, preferably producing a protective immunity against the pathogen which was the origin of the antigen. A number of such systems are available today, however the majority of these are based on membrane components which are proteins.

Most virulent bacteria have carbohydrates on their surface, such as lipopolysaccharides and capsular polysaccharides. Antibodies directed against capsular polysaccharides provide, among other things, enhanced phagocytosis and killing of bacterial cells. Usually there are a number of serotypes of a given bacterial species, for example there are more than 80 known serotypes of *Streptococcus pneumoniae* related to their carbohydrate capsular structures.

Bacterial polysaccharides are classical examples of antigens that are not T helper cell-dependent, and hence, if they are immunogenic at all, they mainly induce IgM class of antibodies. This is so, because only B cells respond to them, and B cells cannot mediate the memory function as opposed to the T cells, which also mediate immunological booster effects.

In immunologically immature small children, elderly and immunosuppressed persons polysaccharides are known to be poor immunogens or not at all immunogenic.

Therefore, polysaccharide antigens which are chemically conjugated to carriers comprising T cell epitopes are effective as vaccines also for the above mentioned immunologically immature children and immunosuppressed adults.

The vaccine-producing industry has long been searching for a general method of producing conjugate-type vaccines. A general and simple method to produce such vaccines would not only be more practical but would also make process and quality control easier.

A method which provides a general method of producing immunogenic products comprising antigenically active carbohydrate moieties and immunologically active carriers, producing useful immunizing components in conjugate-type vaccines is described in WO 97/35613, the contents of which is incorporated herein by reference.

In said International application is described a method of producing an immunogenic product consisting of antigenically active carbohydrate moieties which are each covalently coupled via identical specified divalent bridge groups to immunologically active carriers containing amino groups.

In a preferred embodiment of said invention, the antigenically active carbohydrate moieties of the immunogenic products derive from bacterial O-polysaccharides and/or capsular polysaccharides. Specific examples of such saccharides are those which derive from *Salmonella* serotypes BO and/or DO or from different serotypes of *Streptococcus pneumoniae* capsular polysaccharides or from *Haemophilus influenzae* capsular polysaccharides.

Another carbohydrate moiety, which is of great importance, is the surface carbohydrate from *M. tuberculosis*. This carbohydrate consists of Lipoarabinomannan (LAM) and is the antigenically dominating surface antigen of mycobacteria, and accounts for up to 15 mg/g of the bacterial weight. LAM has profound biologic effects; hence LAM has been reported to interfere with gamma-interferon mediated activation of macrophages, scavenge toxic oxygen free radicals, inhibit protein kinase activity, and induces the expression of macrophage-early genes. LAM has been tested extensively as a possible antigen in vaccine formulations for a long time, however only by parenteral administration, resulting in poor protection in animal experiments.

The immunologically active carriers of the immunogenic product of the conjugate of said invention is preferably derived from polypeptides. In a preferred embodiment said polypeptide is tetanus toxoid, diphtheria toxoid, cholera subunit B or Protein D from *H. influenzae*.

DESCRIPTION OF THE INVENTION

The present invention is directed to a vaccine formulation against a microorganism comprising, as adjuvant, one or more substances selected from a) monoglyceride preparations having at least 80% monoglyceride content and having the general formula

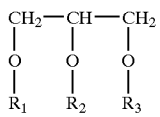

wherein $R_1$ and $R_2$ is H and $R_3$ is one acyl group containing from 6 to 24 carbon atoms, and where the acyl chains may contain one or more unsaturated bonds and b) fatty acids of the general formula

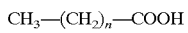

where "n" may be varied between 4 and 22, and where the acyl chain may contain one or more unsaturated bonds, and as immunizing component, an immunogenic product consisting of antigenically active carbohydrate moieties (ACM) derived from said microorganism which are each covalently coupled, possibly via identical divalent bridge groups, to immunologically active carriers (IAC).

In an embodiment of the invention the immunologically active carriers (IAC) contain amino groups and said divalent bridge group has the following structural formula

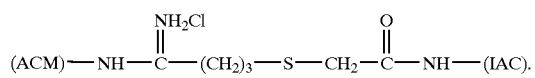

The adjuvant of the vaccine formulation of the invention preferably has a monoglyceride preparation content of at least 90%, preferably at least 95%, and the acyl chains of the monoglyceride preparation contains 8 to 20 carbon atoms, preferably 14 to 20 carbon atoms, and the acyl chains optionally contains one or more unsaturated bonds, and the immunologically active carriers (IAC) are derived from polypeptides and are selected from tetanus toxoid, diphtheria toxoid, cholera subunit B or Protein D from *H. influenzae*.

The vaccine formulation according to the invention may further comprise pharmaceutical excipients selected from the group consisting of biocompatible oils, such as such as rape seed oil, sunflower oil, peanut oil, cotton seed oil, jojoba oil, squalan or squalene, physiological saline solution, preservatives and osmotic pressure controlling agents, carrier gases, pH-controlling agents, organic solvents, hydrophobic agents, enzyme inhibitors, water absorbing polymers, surfactants, absorption promoters, and anti-oxidative agents.

A most preferred embodiment of the invention is a vaccine formulation which comprises, as adjuvant, a mixture of mono-olein and oleic acid, and possibly soybean oil and, as immunizing component, lipoarabinomannan-tetanus toxoid (LAM-TT).

Examples of other antigenically active carbohydrate moieties of the immunogenic products of the immunizing component of the invention derive from bacterial O-polysaccharides and/or capsular polysaccharides. Specific examples of such saccharides are those which derive from *Salmonella* serotypes BO and/or DO or from different serotypes of *Streptococcus pneumoniae* capsular polysaccharides or from *Haemophilus influenzae* capsular polysaccharides.

In another preferred embodiment of the vaccine formulation according to the invention, the formulation is formulated into a preparation for mucosal administration, such as nasal, pulmonary, oral, rectal or vaginal administration.

Another aspect of the invention is directed to an aerosol or spray package comprising a TB vaccine composition according to the invention.

Yet another aspect of the invention is directed to a nose-drop package comprising a TB vaccine composition according to the invention.

A further aspect of the invention is directed to a method of vaccinating a mammal against a microorganism having antigenically active carbohydrate moieties (ACM), which comprises mucosal administration to the mammal of an protection-inducing amount of a TB vaccine composition according to the invention.

As described above the present commercially available vaccine against TB comprises an attenuated strain of the bacteria. Such systems may under certain circumstances, when administered as a vaccine, result in an infection by the attenuated bacteria. Furthermore, antigen systems based on whole bacteria are difficult to standardize according to pharmaceutical regulations. Thus, the preferred system as described in the present invention is a purified antigen from the pathogen, which, in combination with adequate adjuvants results in protective immunity. However, certain antigens, such as carbohydrates, may not generate protective immunity if not associated to a carrier in the form of a conjugate. Furthermore, conjugate vaccines are more stable and consequently more attractive as antigens/vaccines, especially in the developing world.

The present invention describes a formulation that may be prefabricated, and therefore no need for skilled personnel is needed upon nasal administration, thereby eliminating injection systems such as needles and syringes which in developing world often are contaminated and thus is spreading diseases between patients. Furthermore, a device for multi-dose aerosol delivery of a nasal vaccine can easily be constructed in way that no person-to-person infection can occur.

The invention will now be illustrated by way of an example, which, however, is not to be interpreted as limitation to the scope of protection according to the appended claims.

SHORT DESCRIPTION OF THE DRAWING

FIG. 1 shows the results of the testing disclosed in Example 1.

EXAMPLE 1

Protection of C57BL mice from intranasal sub-lethal challenge with *M. tuberculosis* (MT) by immunization with live BCG and heat-killed BCG or lipoarabinomannan-tetanus toxoid (LAM-TT) conjugate in two different L3 lipid adjuvant formulations.

The emulsion was produced by mixing the LAM-TT conjugate with 100 μl of soybean oil and 100 μl of a mixture of mono-olein and oleic acid (1:1). The amount of LAM-TT conjugate was adjusted so that a dose of 10 μg was given to the mice in 100 μl (parenteral) or in 10 μl (nasal). This mixture was sonicated briefly for a few seconds whereupon 1.0 ml of 0.1 M TRIS buffer and 20 μl of 4 M NaOH were added. Sonication was performed for 2 minutes whereupon the emulsion was used for immunization. An L3 suspension was produced from a 1:1 molar mixture of mono-olein and oleic acid (1.43 g mono-olein and 1.12 g oleic acid) which was added to 40 ml of 0.1 M Tris buffer. Before sonication for 2 minutes 640 μl of 4 M NaOH was added. Before immunization the L3 adjuvant was mixed with the LAM-TT conjugate in order to achieve a dose of 10 μg in 100 μl for parenteral injection or 10 μl for nasal administration.

Immunization 1; 0 weeks (parenteral for all groups). Immunization 2; 3 weeks (nasally for all groups except live BCG which was administered parenterally). Challange; 4 weeks.

Changes of body weight (%) related to initial weight at time 0 weeks. Average body weight changes±SE of 10 mice/group are shown in FIG. 1.

As can be seen from the weight changes, both of the adjuvant formulations containing LAM-TT result in a positive body weight development.

What is claimed is:

1. A vaccine formulation against a *Mycobacterium* comprising an adjuvant comprising a) monoglyceride preparations having at least 80% monoglyceride content and having a formula $$\begin{array}{ccc} CH_2 - CH - CH_2 \\ | & | & | \\ O & O & O \\ | & | & | \\ R & R & R \end{array}$$

wherein R is selected from the group consisting of H and an acyl group containing from 6 to 24 carbon atoms with the proviso that two of the R groups are H and b) a fatty acid with 6 to 24 carbon atoms and an immunogenic product consisting of antigenically active carbohydrate moieties (ACM) from *Mycobacterium tuberculosis* which are each covalently coupled, via divalent bridge groups, to immunologically active carriers (IAC).

2. The vaccine formulation according to claim 1, wherein the immunologically active carriers (IAC) contain amino groups and said divalent bridge group has the following structural formula $$LAM - \underset{H}{N} - \overset{NH_2Cl}{\underset{\|}{C}} - (CH_2)_3 - S - CH_2 - \overset{O}{\underset{\|}{C}} - NH - (IAC),$$

wherein LAM is Lipoarabinomannan.

3. The vaccine formulation according to claim 1, wherein the adjuvant has a content of monoglyceride in the monoglyceride preparation of at least 90%, and the acyl chains of the monoglyceride in the monoglyceride preparation contains 8 to 20 carbon atoms, and the immunologically active carriers (IAC) are from polypeptides which are selected from the group consisting of tetanus toxoid, diphtheria toxoid, cholera subunit B and Protein D from *H. influenza*.

4. The vaccine formulation according to claim 3, wherein the adjuvant has a content of monoglyceride in the monoglyceride preparation of at least 95% and the acyl chains of the monoglyceride in the monoglyceride preparation contains 14 to 20 carbon atoms, and the immunologically active carriers (IAC) are from polypeptides which are selected from the group consisting of tetanus toxoid, diphtheria toxoid, cholera subunit B and Protein D from *H. influenza*.

5. The vaccine formulation according to claim 1, which further comprises pharmaceutical excipients selected from the group consisting of biocompatible oils, physiological saline solutions, preservatives, osmotic pressure controlling agents, carrier gases, pH-controlling agents, organic solvents, hydrophobic agents, enzyme inhibitors, water absorbing polymers, surfactants, absorption promoters and anti-oxidative agents.

6. The vaccine formulation according to claim 1, wherein the monoglyceride preparation is mono-olein and the fatty acid is oleic acid, and the immunogenic component is lipoarabinomannan-tetanus toxoid (LAM-TT).

7. The vaccine formulation according to claim 6, wherein the adjuvant further comprises soybean oil.

8. The vaccine formulation according to claim 1, wherein the formulation is formulated into a preparation for mucosal administration.

9. The vaccine formulation according to claim 8, wherein the mucosal administration is for nasal, pulmonary, oral or vaginal administration.

10. The vaccine formulation of claim 1, wherein the antigenically active carbohydrate moieties (ACM) are each covalently coupled via identical divalent bridge groups to the immunologically active carriers (IAC).

11. An aerosol or spray package comprising a vaccine formulation comprising an adjuvant comprising: a) monoglyceride preparations having at least 80% monoglyceride content and having a formula $$\begin{array}{ccc} CH_2 - CH - CH_2 \\ | & | & | \\ O & O & O \\ | & | & | \\ R & R & R \end{array}$$

wherein R is selected from the group consisting of H and an acyl group containing from 6 to 24 carbon atoms with the proviso that two of the R groups are H and b) a fatty acid with 6 to 24 carbon atoms and and an immunogenic product consisting of antigenically active carbohydrate moieties (ACM) from *Mycobacterium tuberculosis* which are each covalently coupled, via divalent bridge groups, to immunologically active carriers (IAC).

12. An aerosol or spray package according to claim 11, wherein the immunologically active carriers (IAC) contain amino groups and said divalent bridge group has the following structural formula $$LAM - \underset{H}{N} - \overset{NH_2Cl}{\underset{\|}{C}} - (CH_2)_3 - S - CH_2 - \overset{O}{\underset{\|}{C}} - NH - (IAC),$$

wherein LAM is Lipoarabinomannan.

13. An aerosol or spray package according to claim 12, wherein the adjuvant has a content of monoglyceride in the monoglyceride preparation of at least 90%, and the acyl chains of the monoglyceride in the monoglyceride preparation contains 8 to 20 carbon atoms, and the immunologically active carriers (IAC) are from polypeptide and are selected from the group consisting of tetanus toxoid, diphtheria toxoid, cholera subunit B and Protein D from *H. influenza*.

14. An aerosol or spray package according to claim 13, wherein the adjuvant has a content of monoglyceride in the monoglyceride preparation of at least 95% and the acyl chains of the monoglyceride in the monoglyceride preparation contains 14 to 20 carbon atoms, and the immunologically active carriers (IAC) are from polypeptides which are selected from the group consisting of tetanus toxoid, diphtheria toxoid, cholera subunit B and Protein D from *H. influenza*.

15. An aerosol or spray package according to claim 12, which further comprises pharmaceutical excipients selected from the group consisting of biocompatible oils, physiological saline solutions, preservatives, osmotic pressure controlling agents, carrier gases, pH-controlling agents, organic solvents, hydrophobic agents, enzyme inhibitors, water absorbing polymers, surfactants, absorption promoters and anti-oxidative agents.

16. An aerosol or spray package according to claim 12, wherein the monoglyceride preparation is mono-olein and the fatty acid is oleic acid, and the immunogenic product is lipoarabinomannan-tetanus toxoid (LAM-TT).

17. An aerosol or spray package according to claim 12, wherein the formulation is formulated into a preparation for mucosal administration.

18. An aerosol or spray package according to claim 17, wherein the mucosal administration is for nasal, pulmonary, oral or vaginal administration.

19. An aerosol or spray package according to claim 16, wherein the adjuvant further comprises soybean oil.

20. The aerosol or spray package of claim 11, wherein the antigenically active carbohydrate moieties (ACM) are each covalently coupled via identical divalent bridge groups to the immunologically active carriers (IAC).

21. A nose-drop package comprising a vaccine formulation comprising an adjuvant comprising: a) monoglyceride preparations having at least 80% monoglyceride content and having a formula $$\begin{array}{ccc} CH_2 & -CH- & CH_2 \\ | & | & | \\ O & O & O \\ | & | & | \\ R & R & R \end{array}$$

wherein R is selected from the group consisting of H and an acyl group containing from 6 to 24 carbon atoms with the proviso that two of the R groups are H and b) a fatty acid with 6 to 24 carbon atoms and and an immunogenic product consisting of antigenically active carbohydrate moieties (ACM) from *Mycobacterium tuberculosis* which are each covalently coupled, via divalent bridge groups, to immunologically active carriers (IAC).

22. The nose-drop package, according to claim 21, wherein the immunologically active carriers (IAC) contain amino groups and said divalent bridge group has the following structural formula $$LAM-\underset{H}{N}-\overset{NH_2Cl}{\underset{\|}{C}}-(CH_2)_3-S-CH_2-\overset{O}{\underset{\|}{C}}-NH-(IAC),$$

wherein LAM is Lipoarabinomannan.

23. The nose-drop package according to claim 21, wherein the adjuvant has a content of monoglyceride in the monoglyceride preparation of at least 90% and the acyl chains of the monoglyceride in the monoglyceride preparation contains 8 to 20 carbon atoms, and the immunologically active carriers (IAC) are from polypeptides which are selected from the group consisting of tetanus toxoid, diphtheria toxoid, cholera subunit B OF and Protein D from *H. influenza*.

24. The nose-drop package according to claim 23, wherein the adjuvant has a content of monoglyceride in the monoglyceride preparation of at least 95% and the acyl chains of the monoglyceride in the monoglyceride preparation contains 14 to 20 carbon atoms, and the immunologically active carriers (IAC) are from polypeptides which are selected from the group consisting of tetanus toxoid, diphtheria toxoid, cholera subunit B and Protein D from *H. influenza*.

25. The nose-drop package according to claim 21, which further comprises pharmaceutical excipients selected from the group consisting of biocompatible oils, physiological saline solutions, preservatives, osmotic pressure controlling agents, carrier gases, pH-controlling agents, organic solvents, hydrophobic agents, enzyme inhibitors, water absorbing polymers, surfactants, absorption promoters and anti-oxidative agents.

26. An nose-drop package according to claim 21, wherein the monoglyceride preparation is mono-olein and the fatty acid is oleic acid, and the immunogenic product is lipoarabinomannan-tetanus toxoid (LAM-TT).

27. The nose-drop package according to claim 21, wherein the formulation is formulated into a preparation for mucosal administration.

28. The nose-drop package according to claim 27, wherein the mucosal administration is for nasal, pulmonary, oral or vaginal administration.

29. The nose-drop package according to claim 26, wherein the adjuvant further comprises soybean oil.

30. The nose-drop package of claim 21, wherein the antigenically active carbohydrate moieties (ACM) are each covalently coupled via identical divalent bridge groups to the immunologically active carriers (IAC).

31. A method of vaccinating a mammal against a Mycobacterium comprising mucosally administering to the mammal of a protection-inducing amount of a vaccine formulation comprising an adjuvant comprising: a) monoglyceride preparations having at least 80% monoglyceride content and having a formula $$\begin{array}{ccc} CH_2 & -CH- & CH_2 \\ | & | & | \\ O & O & O \\ | & | & | \\ R & R & R \end{array}$$

wherein R is selected from the group consisting of H and an acyl group containing from 6 to 24 carbon atoms with the proviso that two of the R groups are H and b) a fatty acid with 6 to 24 carbon atoms and and an immunogenic product consisting of antigenically active carbohydrate moieties (ACM) from *Mycobacterium tuberculosis* which are each covalently coupled, via divalent bridge groups, to immunologically active carriers (IAC).

32. The method of vaccinating a mammal against mycobacterium according to claim 31, wherein the immunologically active carriers (IAC) contain amino groups and said divalent bridge group has the following structural formula

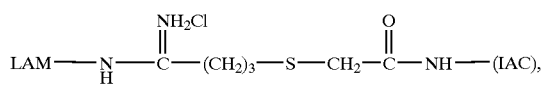

wherein LAM is Lipoarabinomannan.

33. The method of vaccinating a mammal against *Mycobacterium* according to claim 31, wherein the adjuvant has a content of monoglyceride in the monoglyceride preparation of at least 90% and the acyl chains of the monoglyceride in the monoglyceride preparation contains 8 to 20 carbon atoms and the immunologically active carriers (IAC) are from polypeptide and are selected from the group consisting of tetanus toxoid, diphtheria toxoid, cholera subunit B or Protein D from *H. influenza*.

34. The method of vaccinating a mammal against mycobacterium according to claim 31, wherein the adjuvant has a content of monoglyceride in the monoglyceride preparation of at least 95% and the acyl chains of the monoglyceride in the monoglyceride preparation contains 14 to 20 carbon atoms and the immunologically active carriers (IAC) are from polypeptides which are selected from the group consisting of tetanus toxoid, diphtheria toxoid, cholera subunit B of and Protein D from *H. influenza*.

35. The method of vaccinating a mammal against mycobacterium according to claim 31, wherein the vaccine further comprises pharmaceutical excipients selected from the group consisting of biocompatible oils, physiological saline solutions, preservatives, osmotic pressure controlling agents, carrier gases, pH-controlling agents, organic solvents, hydrophobic agents, enzyme inhibitors, water absorbing polymers, surfactants, absorption promoters and anti-oxidative agents.

36. The method of vaccinating according to claim 31, wherein the monoglyceride preparation is mono-olein and the fatty acid is oleic acid, and the immunogenic product is lipoarabinomannan-tetanus toxoid (LAM-TT).

37. The method of vaccinating a mammal against mycobacterium according to claim 31, wherein the formulation is formulated into a preparation for mucosal administration.

38. The method of vaccinating a mammal against mycobacterium according to claim 37, wherein the mucosal administration is for nasal, pulmonary, oral or vaginal administration.

39. The method of vaccinating a mammal against mycobacterium according to claim 36, wherein the adjuvant further comprises soybean oil.

40. The method of vaccinating of claim 31, wherein immunizing product consists of antigenically active carbohydrate moieties (ACM) are each covalently coupled via identical divalent bridge groups to the immunologically active carriers (IAC).

* * * * *